United States Patent [19]

Anderson et al.

[11] Patent Number: 4,939,159
[45] Date of Patent: Jul. 3, 1990

[54] AZAINDOLE DERIVATIVES USEFUL AS CHOLESTEROL BIOSYNTHESIS INHIBITORS

[75] Inventors: Paul L. Anderson, Randolph; Faizulla G. Kathawala, Mountain Lakes; Nicholas A. Paolella, Livingston; Sompong Wattanasin, Hopatcong, all of N.J.

[73] Assignee: Sandoz Pharm. Corp., E. Hanover, N.J.

[21] Appl. No.: 320,664

[22] Filed: Mar. 8, 1989

Related U.S. Application Data

[63] Continuation-in-part of Ser. No. 165,656, Mar. 8, 1988, abandoned, which is a continuation of Ser. No. 905,897, Sep. 10, 1986, abandoned.

[51] Int. Cl.⁵ .................. A61K 31/435; C07D 471/04
[52] U.S. Cl. ..................................... 514/300; 546/113
[58] Field of Search ......................... 546/113; 514/300

[56] References Cited

PUBLICATIONS

Chem. Abstracts, vol. 102, 24475 (1985).

Primary Examiner—Mary C. Lee
Assistant Examiner—Bernard I. Dentz
Attorney, Agent, or Firm—Gerald D. Sharkin; Richard E. Vila; Joanne M. Giesser

[57] ABSTRACT

Compounds of the formula I:

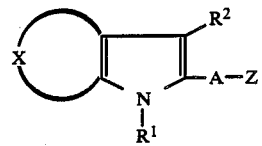

wherein
X is the residue of an unsubstituted 6-membered aromatic ring having 3 carbon atoms and one nitrogen atom;
$R^1$ is $C_{1-6}$ primary alkyl (free of asymmetric carbon atoms), or isopropyl;
$R^2$ is substituted or unsubstituted phenyl, primary or secondary $C_{1-6}$ alkyl (free of asymmetric carbons), $C_{3-6}$ cycloalkyl or phenalkyl as defined in the Specification

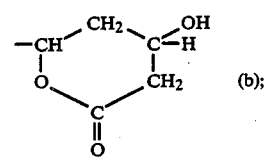

in which $R^8$ is hydrogen, $R^9$ or M,
wherein
$R^9$ is a physiologically acceptable and hydrolyzable ester group, and
M is a pharmaceutically acceptable cation;
are obtained by multi-step processes and are useful as cholesterol biosynthesis inhibitors.

28 Claims, No Drawings

AZAINDOLE DERIVATIVES USEFUL AS CHOLESTEROL BIOSYNTHESIS INHIBITORS

This is a continuation-in-part of application Ser. No. 07/65,656, filed Mar. 8, 1988, now abandoned, which is a continuation of application Ser. No. 06/905,897, filed Sept. 10, 1986, and now abandoned.

This invention pertains to organic compounds, and more particularly to 7-(azaindol-2-yl)-hept-6-enoic acid derivatives as well as to the use of such compounds and pharmaceutical compositions containing such compounds, as well as to intermediates and methods of preparation.

The final compounds involved in the invention may be conveniently represented by formula I:

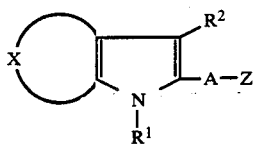

wherein
X is

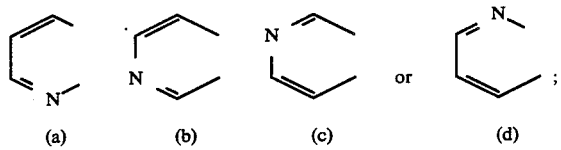

$R^1$ is a primary $C_{1-6}$alkyl not containing an asymmetric carbon atom; or isopropyl;
$R^2$ is

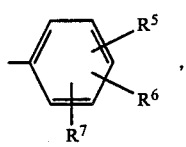

(b) a primary or secondary $C_{1-6}$alkyl not containing an asymmetric carbon atom, (c) $C_{3-6}$cycloalkyl or (d) phenyl—$(CH_2)m$—,
wherein
$R^5$ is hydrogen, $C_{1-3}$alkyl, n-butyl, i-butyl, t-butyl, $C_{1-3}$alkoxy, n-butoxy, i-butoxy, trifluoromethyl, fluoro, chloro, phenoxy or benzyloxy;
$R^6$ alkyl, $C_{1-3}$alkoxy, trifluoromethyl, fluoro, chloro, phenoxy or bernzyloxy;
$R^7$ is hydrogen, $C_{1-2}$alkyl, $C_{1-2}$alkoxy, fluoro or chloro; and
m is 1, 2 or 3;
with the provisos that not more than one of $R^5$ and $R^6$ is trifluoromethyl, not more than one of $R^5$ and $R^6$ is phenoxy, and not more than one of $R^5$ and $R^6$ is benzyloxy;

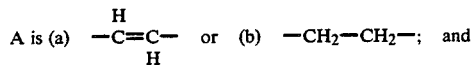

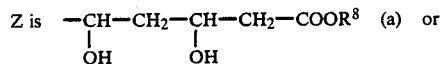

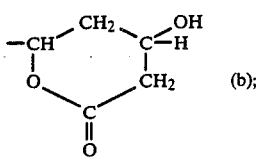

in which $R^8$ is hydrogen, $R^9$ or M,
wherein
$R^9$ is a physiologically acceptable and hydrolyzable ester group, and
M is a pharmaceutically acceptable cation.

Compounds I may be viewed as consisting of various sub-classes depending upon the definition of their variable portions. Compounds I may be of the following subclasses depending on the nature of Z;

| Designation: | Z= | Nature |
| --- | --- | --- |
| Compounds I1 | type (a); $R^8$ = H, | free acid |
| Compounds I2 | type (a); $R^8$ = $R^9$ | ester |
| Compounds I3 | type (a); $R^8$ = M | salt |
| Compounds I4 | type (b) | lactone |

Furthermore, Compounds I may be classified according to the location of the nitrogen atom in the X- moiety;

| Designation: | X is of type |
| --- | --- |
| Compounds Ia | (a) |
| Compounds Ib | (b) |
| Compounds Ic | (c) |
| Compounds Id | (d) |

A preferred type of Compounds I is designated I' where $R^1$ is alkyl, especially methyl or isopropyl, A is (a); and $R^2$ is an aryl group i.e. (a), especially p-fluorophenyl, phenyl or 3,5-dimethylphenyl, and particularly p-fluorophenyl.

Compounds Id and Ia are generally preferred over Compounds Ib and Ic. Particularly preferred are Compounds I'd and I'a where R' is alkyl, especially methyl or isopropyl, A is (a), and $R^2$ is an aryl group, i.e. (a), especially p-fluorophenyl, phenyl or 3,5-dimethylphenyl and particularly p-fluorophenyl.

When X is (b) or (d), the preferred compounds are I'b and Id where $R^1$ is alkyl, especially methyl or isopropyl, A is (a), and $R^2$ is an aryl group, i.e. (a), especially p-fluorophenyl, phenyl or 3,5-dimethylphenyl and particularly p-fluorophenyl.

When $R^8$ is $R^9$, it is preferably ethyl, and when it is M, it is preferably sodium, potassium, magnesium or calcium, especially sodium.

By the term "physiologically acceptable and hydrolyzable ester group" is meant a group which, together with the —COO— radical to which it is attached, forms an ester group which is physiologically acceptable and hydrolyzable under physiological conditions to yield a compound of Formula I wherein R8 is hydrogen and an alcohol which itself is physiologically acceptable, i.e., non-toxic, at the desired dosage level, and which, preferably, is free of centers of asymmetry. Examples of such groups are $C_{1-3}$alkyl, n-butyl, i-butyl, t-butyl and benzyl, collectively referred to as $R^{9'}$.

A particular subclass of Compounds I is Compounds I2″ in which $R^8$ is $R^{9'''}$, i.e. $C_{1-4}$ primary alkyl, especially ethyl.

Compounds I may further be viewed as two subclasses depending on the nature of A, i.e. I° where (A=a) and $I^x$ where (A=b), the former being preferred.

(Scheme A) and another involving a Wittig reagent (Scheme B).

Scheme A is represented below in Reaction Scheme A in which X, $R^1$, and $R^2$ and R are as defined above, Ak and Ak' are, independently, alkali metal cations, especially Li +; and $R^{10}$ is lower alkyl, e.g. unbranched $C_{1-4}$alkyl, e.g. ethyl, $R^{15}$ is a primary or secondary $C_2$-$C_4$alkyl, e.g. ethyl; and $R^{16}$ is allyl or $C_1$-$C_4$alkyl, preferably not tertiary, e.g. methyl.

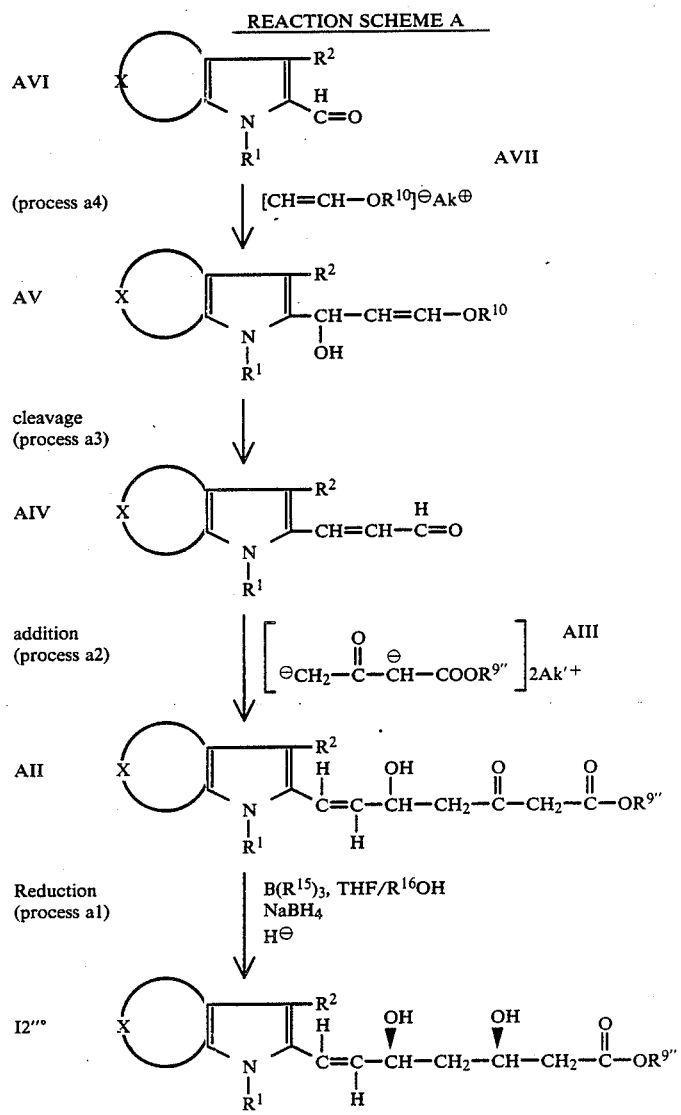

As is well known in the art, ester, free acid and salt forms of an organic acid are interconvertible. Hence, where an ester form (here I2) is prepared, it can then be saponified to its corresponding salt (I3) which can be neutralized to the free acid form (I1), which can be cyclized to the corresponding lactone (I4), and the reverse; all by adapting conventional processes. Accordingly, preparation of an ester I2 where $R^8$ is $R^{9'''}$, i.e. I2″, provides a compound of the invention, as well as a source of the corresponding other forms of Compounds I.

Compounds I2‴° i.e. Compounds I in which A is (a), Z is (a), and $R^8 = R^{9'''}$ are obtainable by either of a series of reaction steps; one series involving a dianion reagent, An alternative scheme (B) is represented below in Reaction Scheme B, wherein X, $R^1$, $R^2$ and $R^{9'''}$ are as defined above, and P1 is a protective group, e.g. a trisubstituted silyl radical having 2 or 3 bulky radicals; the bulky radicals being independently selected from the group consisting of (a) $C_4$-$C_8$ tertiary alkyl, e.g. t.-butyl, and (b) phenyl which may be unsubstituted or substituted by up to two $C_1$-$C_4$alkyl, chloro, nitro or trifluoromethyl substituents or monosubstituted in the para-position by phenyl or benzyl, which may be unsubstituted or substituted by one or two of said alkyl, chloro, nitro or trifluoromethyl substituents, and the non-bulky radicals being $C_{1-4}$ unbranched alkyl, (a preferred group is diphenyl-t-butylsilyl) and Et is ethyl.

In process (b2), reagents BIII are obtainable as described in U.S. Pat. No. 4,571,428 (issued Feb. 18, 1986), which patent is incorporated herein by reference. The proportion of threo to erythro forms of Compounds BIII is carried through in products BII and I2'''°. The erythro form is preferred. Also, chiral characteristics of a Compound BIII will result in products of corresponding enantiomeric identity. Hence, particular enantiomers of Compounds I are thus obtainable. Preparation of Compounds BIII in the 3R,5S- form are disclosed in application Ser. No. 857,689 (filed Apr. 30, 1986), now abandoned, and parent of application serial number 07/166,594, filed Mar. 10, 1988, now U.S. Pat. No. 4,870,199, issued Sept. 26, 1989 which is incorporated herein by reference.

below in Reaction Scheme C, in which X, $R^{1'}$ and $R^2$ are as defined above, and L is a leaving group.

Leaving groups are well known in the art, and include higher halo, i.e, chloro, bromo, or iodo, preferably chloro, and alkyl- and aryl-sulfonyl radicals, e.g., $C_1$-$C_6$alkyl or phenyl which may be unsubstituted or monosubstituted by a $C_1$-$C_4$alkyl, such as p-toluenesulfonyl.

1-Isopropyl analogs of compounds AVIc1, i.e. compounds AVIc2 which are compounds AVI in which X and $R^2$ are as defined and $R^1$ is isopropyl, are obtainable by applying sequentially the procedures of processes (c2) and then (c1) starting with analogs of compounds CIII in which $R^1$ is isopropyl, i.e. CIIIe; such compounds being obtainable by the procedure of Reaction

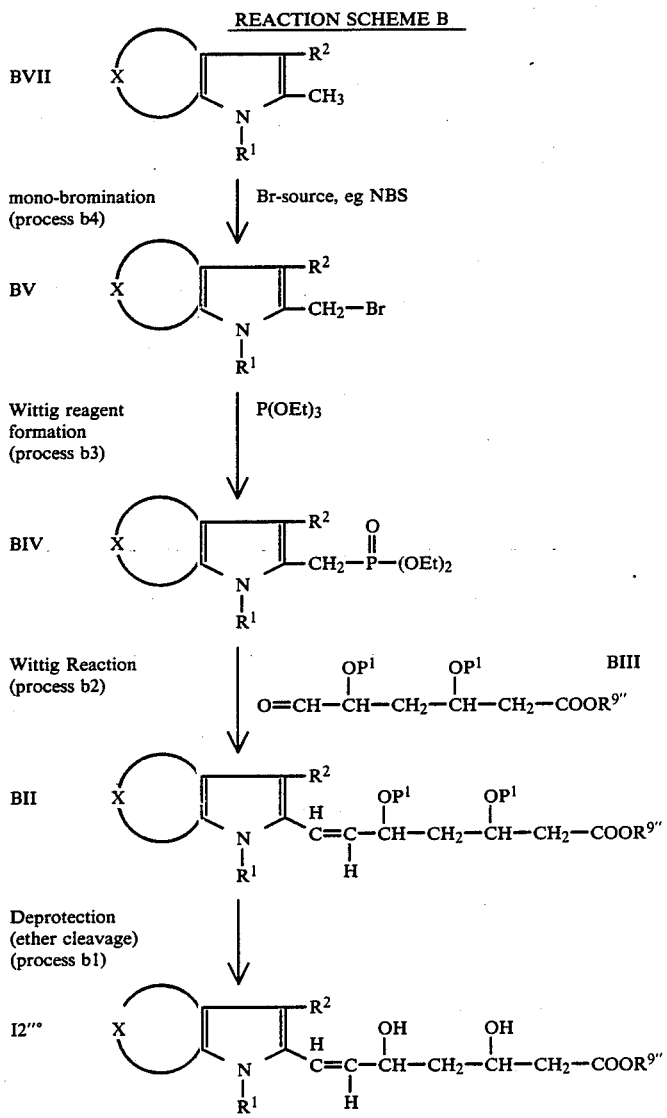

2-Formyl-bearing Compounds AvI are obtainable from their 2-dibromomethyl analogues (compounds CII) by hydrolysis in the presence of an acid acceptor. Preparation of compounds AYIc1, i.e. those compounds AYI in which X and $R^2$ are as defined above, and $R^1$ is $R^{1'}$ which is the same as $R^1$ except isopropyl, i.e. it is primary alkyl having from 1 to 6 carbon atoms not containing an asymmetric carbon atom is represented Scheme E hereinafter presented. It will be noted that compounds CIII+CIIIe=compounds BVII.

REACTION SCHEME C

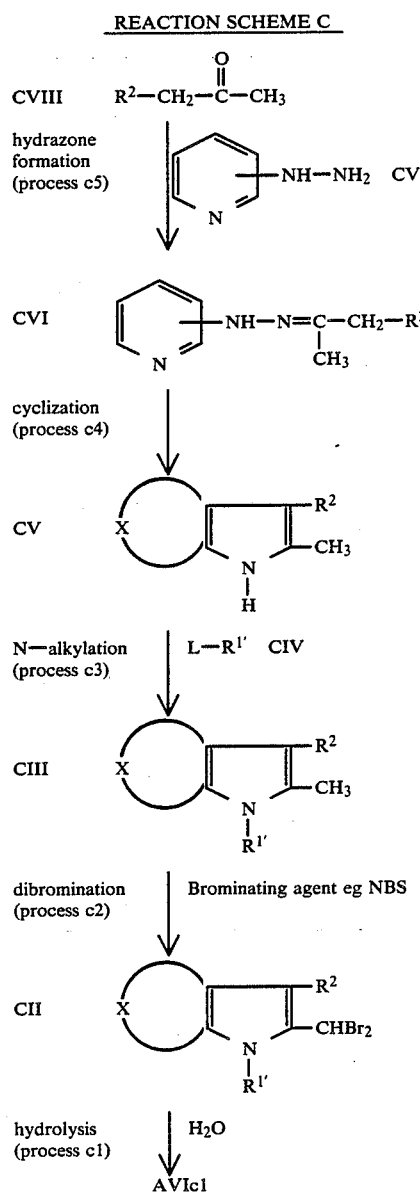

Compounds AvI in which $R^1$ is alkyl, for example, Compounds AvId, are obtainable by formylating a 2-unsubstituted analog. Compounds AvId are conveniently obtained as described in Reaction Scheme D, below, in which L, $R^2$ and X are as defined above, and $R^{14}$ is a $C_{1-4}$ unbranched alkyl.

REACTION SCHEME D

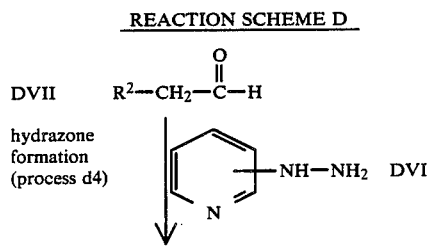

-continued
REACTION SCHEME D

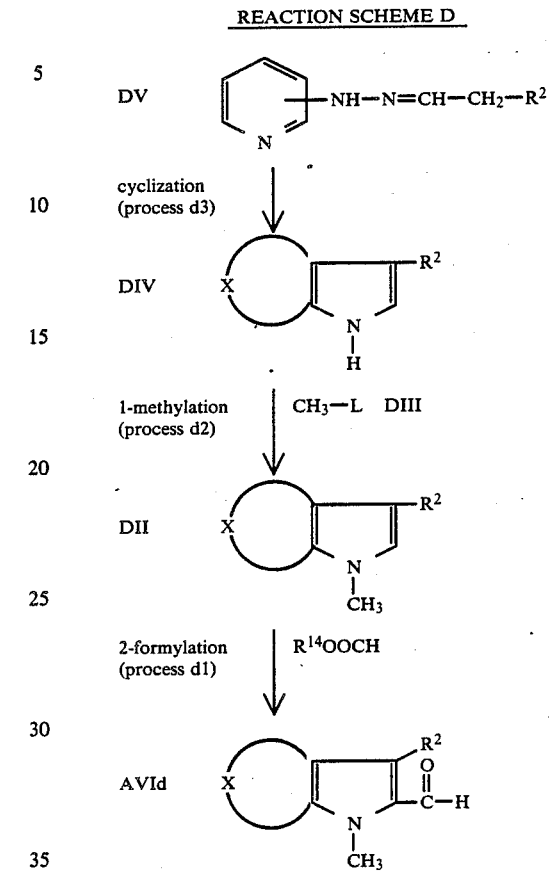

Compounds BvII in which $R^1$ is isopropyl, i.e. Compounds CIIIe, are obtainable by a series of reaction steps as represented in Reaction Scheme E, below, in which X and $R^2$ are as defined above and Y is the leaving portion of an acetylating agent, such as chloro for acetyl chloride, or $O-COCH_3$ acetic acid anhydride.

REACTION SCHEME E

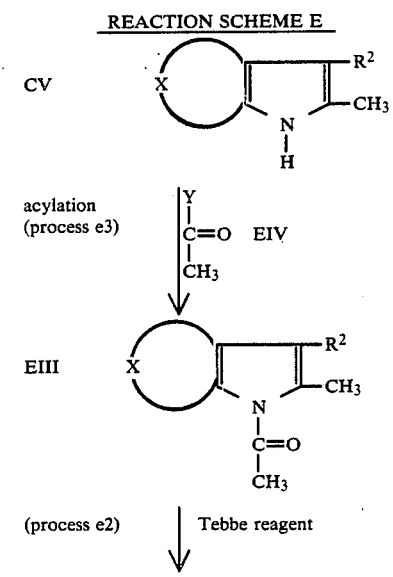

-continued
REACTION SCHEME E

EII 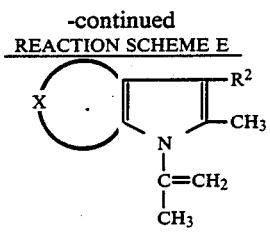

hydrogenation (process e1) ↓ H₂

CIIIe 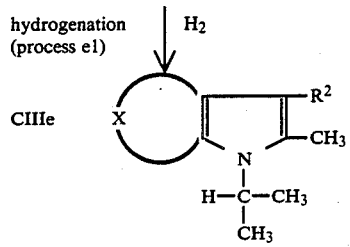

An alternative method of preparing compounds AVIf which are compounds AvI in which R¹ is isopropyl and R² is as defined above, is represented in Reaction Scheme F, below, in which R²,X, Y, L and Et are as defined above, and P² is either the same as P¹ as defined, above, or a tri(C₁₋₄)-alkylsilyl group such as trimethylsilyl.

REACTION SCHEME F

FIX    R²—CH₂—Br

Grignard reagent formation (process f9) | magnesium metal/ether ↓

FVIII    R²—CH₂—MgBr (process f8) ↓ 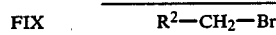

↓ aq. HCl

↓ distillation

Hydrazone formation (process f7) ↓ 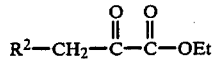

FVII 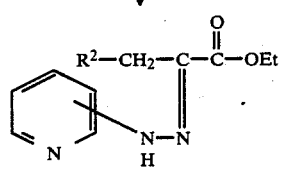

cyclization (process f6) ↓

-continued
REACTION SCHEME F

FVI 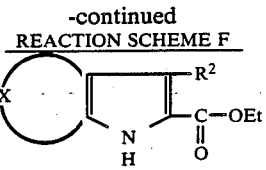

Reduction (process f5) ↓

FV 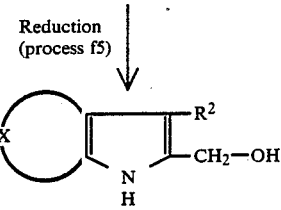

Protection (process f4) ↓ P²—L

FIV 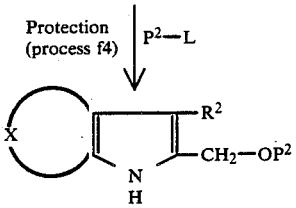

1-isopropyl formation (process f3) ↓ CH₃C—Y  Tebbe reagent [H]

FIII 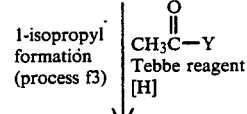

Deprotection (process f2) ↓

FII 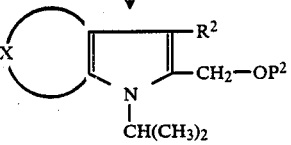

oxidation (process f1) ↓

AVIf 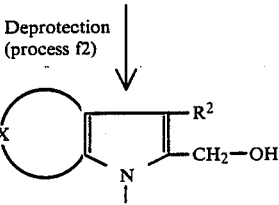

With reference to Reaction Scheme F, above:

Process (f1) may be carried out in a conventional manner for oxidizing a primary alcohol to an aldehyde, e.g., using manganese dioxide in toluene.

Process (f2) is analogous to process (b1) in Table B, below.

Process (f3) is analogous to process (e3), (e2) and (e1) in Table E, below.

Process (f4) may be carried out in a conventional manner for protecting an alcohol, e.g. treating with trimethylsilyl chloride.

Process (f5) may be carried out in a conventional manner for reducing an ester to an alcohol, e.g., using lithium aluminum hydride in tetrahydrofuran.

Process (f6) is analogous to process (c4) in Table C, below.

Process (f7) is analogous to process (c5) in Table C, below.

Processes (f8) and (f9) may be carried out by conventional methods for utilization and preparation of Grignard reagents.

Compounds $I^x$ (i.e. compound I where A=b) are conveniently obtained by saturating the olefinc unit of a corresponding compound A II (process g1) and then reducing the product (a compound G II) in a manner analogous to process a1 (above). Such a procedure is represented in Reaction Scheme G, below in which X, $R^1$, $R^2$, $R^{9'''}$, $R^{15}$ and $R^{16}$ are as defined above.

REACTION SCHEME G

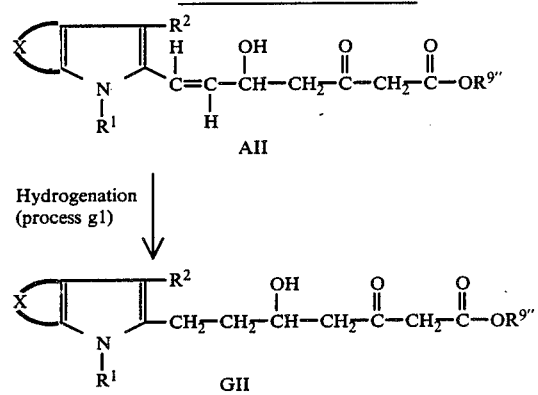

-continued
REACTION SCHEME G

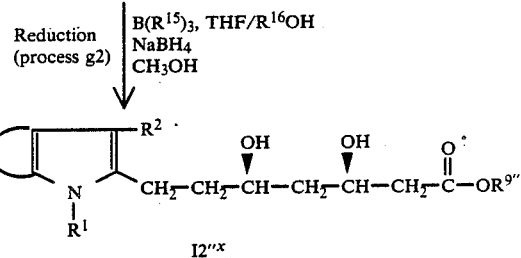

Process (g1) may be carried out in the conventional manner for hydrogenating a ethylenically unsaturated bond, under conditions that do not alter the remainder of the compounds; for example at about 20° to 40° C., e.g R.T. under a pressure of about 40 to 50 p.s.i. of hydrogen gas in the presence of a hydrogenation catalyst e.g, 5% palladium on charcoal or 5% rhodium on charcoal, i.e. an inert medium, e.g. a lower alkanol, such as ethanol.

Alternatively, a compound $12'''°$ or BII can be reduced by the procedure of process (g1) to obtain its corresponding saturated analog (a compound $12''^x$ or $BII^x$).

REACTION SCHEME H

Reaction Scheme H is the preferred way of making compounds of formulae I where X is c, AvI, etc.

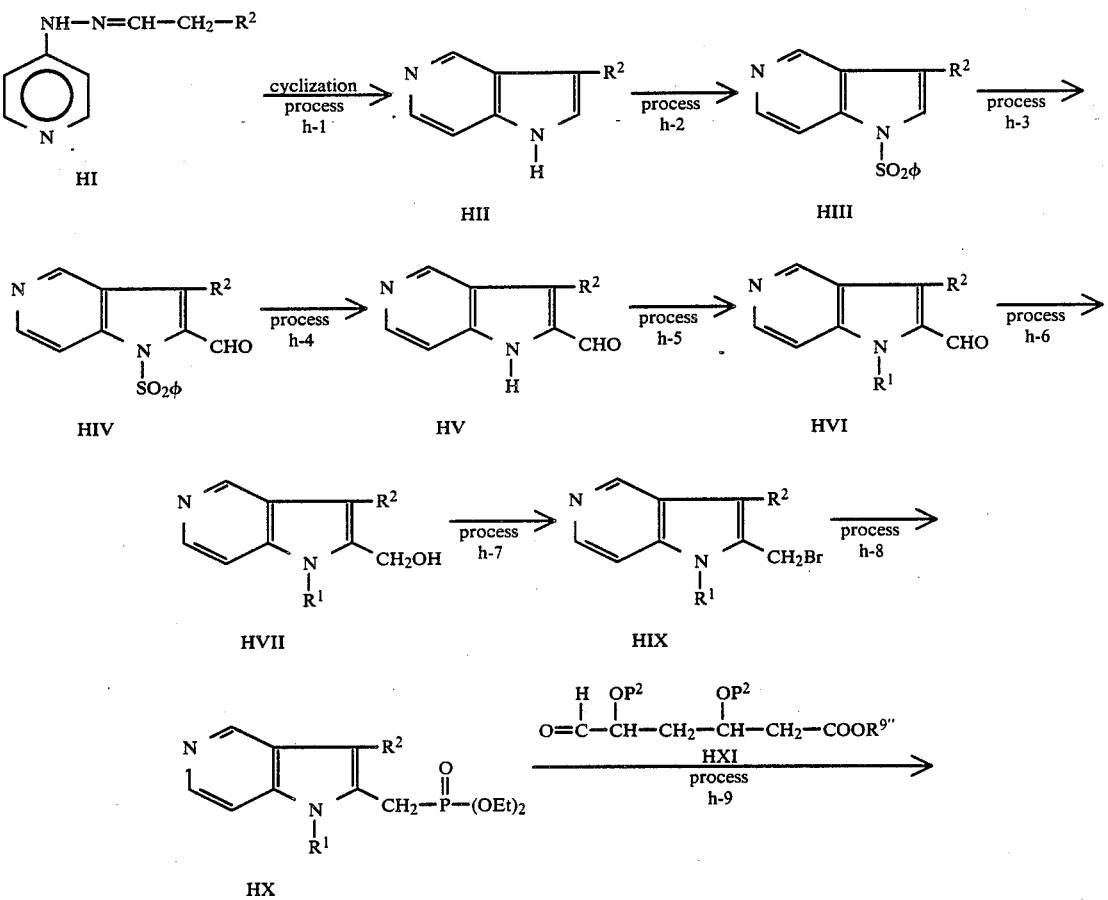

-continued

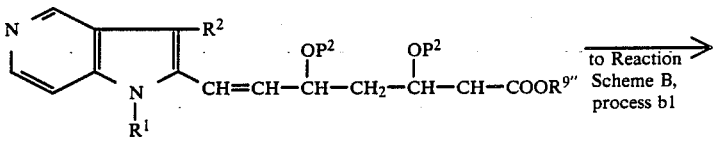

HXII

The parameters applicable to the processes illustrated in the Reaction Schemes, above, are listed in the following tables, in which general parameters are described with preferences as examples. In processes in which a medium is employed, it is understood that the medium is an inert solvent under the reaction conditions and is essentially anhydrous, i.e. moisture-free, if essentially anhydrous conditions are called for. Where anhydrous conditions are called for, it is preferred that such reaction be carried out in an inert atmosphere e.g. under dry nitrogen gas.

In the tables, Q indicates an alkali metal salt usually used in situ, and []indicates an adduct or complex reaction product which is reacted in a subsequent quenching step usually, quenched to hydrolyze or decompose it. Where a quenching step is employed, water is used, but often as an aqueous solution, e.g. saturated aqueous $NH_4Cl$.

The Tebbe reagent used in process (e2) may be prepared as described in J. Am. Chem. Soc. 102, 3270, (1980).

Except as noted below, all of the process steps in the preparation of the compounds of this invention are known for carrying out reactions on analogous materials in a conventional manner.

The procedure for introducing an isopropyl group onto a nucleus is novel (in Reaction Schemes E and F) and does not constitute part of this invention.

Likewise, process (a1) is novel and does not form part of this invention. In an alternative method of carrying out process (a1) in place of a trialkyloorane reagent there may be used an equivalent amount of a monoalkoxydialkylborane of the formula Gk:

Gk  $R^{17}O-B(R^{15})_2$ in which $R^{15}$ is as defined above and $R^{17}$ is allyl or a lower alkyl having from 1 to 4 carbon atoms, preferably not tertiary. $R^{15}$, $R^{16}$ and $R^{17}$ may be the same, but need not be. Preparation of compounds Gk are described by Koster et al, Ann., 1975, 352. $R^{17}$ is preferably methyl.

TABLE A

| | Process Step |
|---|---|
| a1 Reduction (3 stages) | |
| Reactants | (1) AII + B(R$^{15}$)$_3$ eg R$^{15}$ = ethyl, in a ratio of about 1:1.02 to 1.3 → [ ]. |
| | (2) NaBH$_4$ + CH$_3$OH + [ ] → [ ]'. |
| | (3) [ ]' + H$^{\oplus}$, eg acetic acid, → I2'''°. |
| Medium | (1) THF/R$^{16}$OH, eg, R$^{16}$ = methyl; ratio = 3 to 6:1, eg 3–4:1. |
| | (1) = (2) = (3). |
| Temperature | (1) 0 to 40°, eg R.T. |
| | (2) −100 to −40°, eg −75° to −78°. |
| | (3) −100 to −40°, eg −75°, then to R.T. |
| Conditions | Essentially anhydrous for (1) + (2). Optionally, air may be bubbled through reaction mixture in (1). |
| a2 Addition via dianion (3 stages) | |
| Reactants | (1) 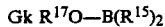 eg ethyl acetoacetate, + |

TABLE A-continued

| | Process Step |
|---|---|
| | Ak (alkali source), eg LDA → AIII. |
| | (2) AIII + AIV → [ ]. |
| | (3) [ ] + quench, eg saturated aqueous NH$_4$Cl → AII. |
| Medium | (1) cyclic ether, eg THF. |
| | (1) = (2) = (3). |
| Temperature | (1) −60 to −20°, eg −40°. |
| | (2) −60° to −20°, eg −40°. |
| | (3) R.T. |
| Conditions | Essentially anh. for (1) + (2). |
| a3 Cleavage (2 stages) | |
| Reactants | (1) AV + acid, eg p-toluenesulfonic acid + H$_2$O → [ ]. |
| | (2) [ ] + quench, eg 10% aq. NaHCO$_3$, → AIV. |
| Medium | (1) Aq. cyclic ether, eg 90% aq. THF. |
| Temperature | (1) 0 to 80°, eg RT; (1) = (2). |
| Conditions | — |
| a4 Addition of olefinic unit | |
| Reactants | (1) BrCH=CH—OR$^{12}$, eg R$^{12}$ = ethyl, + Ak (alkali source), eg t-butyllithium, → AVII. |
| | (2) AVI + AVII → [ ]. |
| | (3) [ ] + quench, eg sat. aq. NH$_4$Cl, → AV. |
| Medium | (1) cyclic ether, eg THF; (1) = (2). |
| Temperature | (1) −40 to −100°, eg about −70°; (1) = (2). |
| Conditions | Essentially anhydrous for (1) + (2). |

TABLE B

| | Process Step |
|---|---|
| b1 Deprotection (when each P$^1$ is a trisubstituted silyl group) | |
| Reactants | BII + tetrabutylammonium fluoride/glacial acetic acid → I2'''°. |
| Medium | cyclic ether, eg THF. |
| Temperature | 0 to 50°, eg R.T. |
| Conditions | Essentially anh. |
| b2 Wittig Reaction (2 stages) | |
| Reactants | (1) BIV + LDA → [ ] |
| | (2) [ ] + BII → [ ] |
| | (3) [ ] + quench, eg sat. sq. NH$_4$Cl → BII. |
| Medium | (1) cyclic ether, eg THF; (1) = (2). |
| Temperature | (1) −10 to −50°, eg −30°. |
| | (2) as (1) |
| | (3) R.T. |
| Conditions | (1) Essentially anh. |
| | (2) " |
| | (3) " |
| b3 Wittig reagent formation | |
| Reactants | BV + P(OC$_2$H$_5$)$_3$ → BIV |
| Medium | THF |
| Temperature | 100 to 140° eg 140°. |
| Conditions | Essentially anh. |
| b4 monobromination | |
| Reactants | BVII + brominating agent, eg N-bromosuccinimide → BV. |
| Medium | halogenated lower aliphatic hydrocarbon, eg CCl$_4$. |
| Temperature | 60 to 100° eg 80°. |
| Conditions | In presence of peroxidic catalyst e.g. benzoyl peroxide + active light, eg incandescent |

TABLE B-continued

| Procss Step | |
|---|---|
| | lamp. Essentially anhydrous. |

TABLE C

| Process Step | |
|---|---|
| c1 Hydrolysis | |
| Reactants | CII + $H_2O$ and acid acceptor, eg calcium carbonate. |
| Medium | aqueous lower alcohol, eg 70% aq. ethanol |
| Temperature | 40° to 120°, eg reflux. |
| Conditions | — |
| c2 Dibromination | |
| Reactants | CIII + brominating agent, - eg NBS → CII. |
| Medium | same as b4. |
| Temperature | same as b4. |
| Conditions | same as b4, but more vigorous and/or longer time, and larger amount of brominating agent. |
| c3 N-alkylation (2 stages) | |
| Reactants | (1) CV + M' (alkali metal source), eg NaH → Q. |
| | (2) Q + CIV, eg L = iodo → CIII. |
| Medium | (1) high-boiling liquid aromatic hydrocarbon, eg xylene; (1) = (2). |
| Temperature | (1) 100 to 150°, eg reflux. (1) = (2). |
| Conditions | (1) essentially anh. (1) = (2). |
| c4 Cyclization | |
| Reactant | CVI → CV. |
| Medium | inert high-boiling liquid solvents, eg diethylene glycol, ie 2-hydroxyethyl ether. |
| Temperature | 200 to 250°, eg reflux. |
| Conditions | Essentially anh. |
| c5 Hydrazone formation | |
| Reagents | CVII + CVIII → CVI. |
| Medium | neat, then toluene used for azeotroping water. |
| Temperature | initiate at 50 to 100°, eg 80 to 90, then refluxing in toluene. |
| Conditions | essentially anh. |

TABLE D

| Process Step | |
|---|---|
| d1 Formylation (3 stages) | |
| Reactants | (1) DII + alkali metal source, eg Li-n-butyl, → Q. |
| | (2) Q + $R^{14}$—OOCH → [ ]. |
| | (3) [ ] + quench, eg sat. aq. $NH_4Cl$ → AVId. |
| Medium | (1) cyclic ether, eg THF; (1) = (2). |
| Temperature | −30 to −60°, eg (1) −40 to −50°; (2) initially = (1), but then warmed to R.T. (3) = 20 to 40°, eg R.T. |
| Conditions | essentially anh. for (1) and (2). |
| d2 Methylation (2 stages) | |
| Reactants | (1) DIV + M″-source, eg NaH → Q. |
| | (2) Q + DIII, eg $CH_3I$ → DII. |
| Medium | same as c3. |
| Temperature | same as c3. |
| Conditions | (1) essentially anh. (1) = (2). |
| d3 Cyclization | |
| Reactant | DV → DIV. |
| Medium | same as c4. |
| Temperature | same as c4. |
| Conditions | essentially anh. |
| d4 Hydrazone formation | |
| Reactants | DVI + DVII → DV. |
| Medium | same as c5. |
| Temperature | same as c5. |
| Conditions | essentially anh. |

TABLE E

| Process Step | |
|---|---|
| e1 | |
| Reactants | EII + $H_2$ → CIIIe |
| Medium | lower alcohol, eg ethanol. |
| Temperature | 20 to 60°, eg R.T. |
| Conditions | under pressure of hydrogen, eg 40–50 psi, in presence of hydrogenation catalyst, eg 5% palladium on carbon. |
| e2 Tebbe reaction (2 stages) | |
| Reactants | (1) EIII + Tebbe reagent → [ ] in presence of pyridine. |
| | (2) [ ] + methanol → EII. |
| Medium | (1) toluene/THF eg 20:1. |
| | (2) same as 1 + diethyl ether. |
| Temperature | (1) −40° then R.T.; (2) 0° then R.T. |
| Conditions | (1) essentially anh. (1) = (2). |
| e3 Acylation | |
| Reactants | CV + EIV → EIII. |
| Medium | none needed where excess of EIV can serve as medium. |
| Temperature | 20 to 100°, eg 100° where EIV is anhydride. |
| Conditions | essentially anh. Where EIV is an acyl halide an acid acceptor, eg triethylamine, is used. |

TABLE F

| Process Step | |
|---|---|
| h-1 cyclization | |
| Reactants: | HI → HII |
| Medium | inert high-boiling liq. solvent eg. DEG, i.e. 2-hydroxyethyl ether |
| Temperature | 200° to 250° C., e.g. reflux |
| Atmosphere | Anhydrous |
| h-2 | |
| Reactants: | 1. HII + n-butyllithium (n-Bu-Li) |
| | 2. Add benzenesulfonyl chloride |
| Medium: | 1. THF; 2. THF |
| Temperature | 1. −80° to −50° C., pref. −78° C. |
| | 2. −80° to −50° C., pref. −78° C. |
| Atmosphere | 1. inert; 2. inert |
| h-3 | |
| Reactants: | 1. HIII + n-BuLi |
| | 2. Add excess ethyl formate |
| Medium: | 1. THF; 2. $HCO_2Et$ |
| Temperature | 1. −50 to −40° C.; −50° to −40°C. |
| Atmosphere | 1. inert; 2. inert |
| h-4 | |
| Reactants: | HIV + $K_2CO_3$ + MeOH |
| Medium | $H_2O$ |
| Temperature | reflux |
| Atmosphere | inert |
| h-5 | |
| Reactants: | 1. HV + 18-Crown-6 + Excess $K^{\oplus}$ $^{\ominus}$O-t-Bu |
| | 2. add 1 equivalent of alkylating agent, e.g. propyl iodide |
| Medium | EtOH |
| Temperature | |
| Atmosphere: | 1. inert; 2. inert |
| h-6 | |
| Reactants: | HVI + $NaBH_4$ |
| Medium | ethanol/diethyl ether |
| Temperature | 20° to 25° C. |
| Atmosphere | inert |
| h-7 | |
| Reactants: | HVII + NBS/dimethyl sulfide → HIX |
| Medium | $CH_2Cl_2$ |
| Temperature | −20° to 0° C. |
| Atmosphere | inert |
| h-8 Wittig reagent formation | |
| Reactants: | HIX + $P(OC_2H_5)_3$ → HX |
| Medium | neat |
| Temperature | 100°–140° C., eg 140° |
| Atmosphere | anhydrous |
| h-9 Wittig reaction | |
| Reagents: | 1. HX + strong base, eg. LDA → [ ] |
| | 2. [ ] + HXI → [ ] |
| | 3. [ ] + quench, e.g. sat. aq. $NH_4Cl$ → HXII |

TABLE F-continued

| | Process Step |
|---|---|
| Medium | 1. cyclic ether, eg THF |
| | 2. as 1. |
| | 3. as 1. |
| Temperature | 1. −10° to −50°, eg −30° |
| | 2. As 1. |
| | 3. R.T. |
| Atmosphere | Anhydrous |

Reagents and starting materials described herein, e.g. compounds BYII, CV, CVI, CVII, CVIII, DIV, DY, DYI, and DvII are known and obtainable by known means, or where not known, may be obtained by adaptation of methods reported in the literature for the preparation of known analogs; some compounds being commercially available.

For example, 1,7-azaindoles (X =a)), and their preparation from 2-pyridylhydrazones is described in Canadian Journal of Chemistry 44, 2455 (1966).

1,4-, 1,5- and 1,6-azaindoles (X =b), (c) and (d), respectively) are reported in the Journal of the Chemical Society 1970, 303.

The final products and intermediate compounds described herein may be recovered and refined, where such is desired, by conventional means, such as by crystallization, distillation or chromatographic techniques, such as column or thin layer chromatography, e.g. silica gel column chromatography.

UTILITY STATEMENT

The compounds of Formula I are competitive inhibitors of 3-hydroxy-3-methylglutaryl coenzyme A (HMG-CoA) reductase, the rate limiting enzyme in cholesterol biosynthesis, and, therefore, they are inhibitors of cholesterol biosynthesis. Consequently, they are useful for lowering the blood cholesterol level in animals, e.g., mammals, especially larger primates such as humans, and, therefore, as hypolipoproteinemic and anti-atherosclerotic agents. The biological activity of the compounds of Formula I may be demonstrated in the following two tests:

Test A. In Vitro Microsomal Assay of HMG-CoA Reductase Inhibition:

This test is known and is carried out as described in column 60 of U.S. Pat. No. 4,613,610, Ser. No. 06/741,903 (filed June 6, 1985) and on page 30 of World (PCT) Published Patent Application 84/02131, both of which are hereby incorporated by reference as if set forth herein in their entirety. The concentration of the test substance (compound of Formula I) in the assay system is 0.0005-2,000 $\mu$ molar. The obtained IC50 is the concentration of the test substance in the assay system observed or calculated to produce a 50% inhibition of HMG-CoA reductase activity.

Test B. In Yivo Cholesterol Biosynthesis Inhibition Test:

This test is also known and is carried out as described in U.S. Pat. No. 4,613,610 and in World (PCT) Published Patent Application 84/02131, both of which are hereby incorporated by reference as if set forth herein in their entirety. In this test the rats are orally administered the test substance (compound of Formula I) at a dose of 0.025-200 mg/kg body weight. The obtained $ED_{50}$ the dose of the test substance observed or calculated to produce a 50% inhibition of $3\beta$-hydroxysterol synthesis.

In Test A, tested compounds of Formula I had $IC_{50}$'s of about 0.02 to 4 $\mu$molar whereas that of Compactin was 1.01 $\mu$molar and that of Mevinolin was 0.14 $\mu$molar. The preferred compound of this application, that of Example 9, had an $IC_{50}$ of 0.0 22 $\mu$molar. In Test B, the compound of Example 9 had an ED50 of 0.0 46 mg/kg. whereas that of Compactin was 3.5 mg/kg. and that of Mevinolin was 0.38 mg/kg.

Since they inhibit cholesterol biosynthesis, the compounds of Formula I (including those of each subgroup thereof) are useful for lowering the blood cholesterol level in animals, e.g., mammals, especially larger primates, in particular humans, and, therefore, as hypolipoproteinemic and anti-atherosclerotic agents.

The precise dosage of the compound of Formula I to be employed for inhibiting cholesterol biosynthesis depends upon several factors including the host, the nature and the severity of the condition being treated, and the mode of administration and the particular active substance (compound of Formula I) employed. However, in general, suitable oral daily dosages of the compounds of Formula I for the satisfactory inhibition or reduction of cholesterol biosynthesis (i.e., the satisfactory reduction of blood cholesterol level and satisfactory treatment of hyperlipoproteinemia and atherosclerosis) are indicated by the test data to be 0.025-100 mg/kg. body weight, e.g., 0.025-5 mg/kg. body weight for the more active compounds. For most larger primates such as humans, a suitable oral daily dosage is indicated to be 0.1-2,000 mg., e.g., 1-140 mg. for the more active compounds. The daily dosage of the compound of Example 9, is indicated to be 0.1-140 mg., e.g. 1-140 mg., preferably 5 to 20 mg., for most larger primates such as humans. For administration by injection, a dosage somehwat lower than would be used for oral administration of the same active substance to the same host having the same condition is usually employed. However, the above dosages are also typically used for I.V. administration.

The daily dosage may be administered in a single dose but more typically is administered in two to four equal portions, typical doses being 0.025-1000 mg. Often, a small dosage is administered initially, and the dosage is gradually increased until the optimal dosage for the host under treatment is determined.

A typical dosage unit for oral administration may contain 0.25-500 mg. of a compound of Formula I.

The compounds of Formula I may be formulated into conventional pharmaceutical compositions and administered by any conventional mode of administration, in particular enterally, e.g., in the form of capsules or tablets, or parenterally, e.g., in the form of sterile injectable solutions or suspensions. The pharmaceutical compositions comprise a compound of Formula I and at least one pharmaceutically acceptable solid or liquid carrier (or diluent). They may be formulated in conventional manner. The compounds of each subgroup thereof may likewise be formulated into such pharmaceutical compositions and administered by such routes.

The compounds of Formula I (including those of each subgroup thereof) may be formulated into such pharmaceutical compositions containing an amount of the active substance that is effective for inhibiting cholesterol biosynthesis in unit dosage form and such compositions comprising at least one solid pharmaceutically acceptable carrier.

A representative formulation suitable for encapsulation in a hard gelatin capsule by conventional techniques is:

| Compound of Formula I, e.g., the compound of | |
|---|---|
| Example 9 | 2 mg. |
| Corn starch | 247 mg. |
| Magnesium stearate | 1 mg. |

As is self-evident to those in the art, each compound of formula I (and every sub-scope and species thereof) has at least two centers of asymmetry (e.g. the two carbon atoms bearing the hydroxy groups in the structure when (Z=a) and the carbon atom bearing the hydroxy group and the carbon atom having the free valence in the structure when (Z=b), and these lead (e.g. with two centers) to four stereoisomeric forms (enantiomers) of each compound (two racemates or pairs of diastereoisomers). The preferred compounds have only two such centers of asymmetry and these four stereoisomers may be designated as the R,R; R,S; S,R; and S,S enantiomers, all four stereoisomers being within the scope of this invention.

The preferred stereoisomers of the compounds of formula I having only two centers of asymmetry wherein (A is a) and (Z is a) are the 3R,5S and 3R,5R isomers and the racemate of which each is a constituent, i.e., the 3R,5S-3S,5R (erythro) and 3R,5R-3S,5S (threo) racemates, with the 3R,5S isomer and the racemate of which it is a constituent being more preferred and the 3R,5S isomer being most preferred.

The preferred stereoisomers of the compounds of formula I having only two centers of asymmetry wherein (A is b) and (Z is a) are the 3R,5R and 3R,5S isomers and the racemate of which each is a constituent, i.e., the 3R,5R-3S,5S (erythro) and 3R,5S-3S,5R (threo) racemates, with the 3R,5R isomer and the racemate of which it is a constituent being more preferred and the 3R,5R isomer being most preferred.

The preferred stereoisomers of the compounds of formula I having only two centers of asymmetry wherein (A is a) and (Z is b) are the 4R,6S and 4R,6R isomers and the racemate of which each is a constituent, i.e., the 4R,6S-4S,6R (trans lactone) and 4R,6R-4S,6S (cis lactone) racemates, with the 4R,6S isomer and the racemate of which it is a constituent being more preferred and the 4R,6S isomer being most preferred.

The preferred stereoisomers of the compounds of formula I having only two centers of asymmetry wherein (A is b) and (Z is b) are the 4R,6R and 4R,6S isomers and the racemate of which each is a constituent, i.e., the 4R,6R-4S,6S (trans lactone) and 4R,6S-4S,6R (cis lactone) racemates, with the 4R,6R isomer and the racemate of which it is a constituent being more preferred and the 4R,6R isomer being most preferred.

The preferences set forth in the preceding four paragraphs also apply to the compounds of formula I having more than two centers of asymmetry and represent the preferred configurations of the indicated positions.

In the Wittig reaction (process b2) of Reaction Scheme B, if in place of a Compound BIII there is employed a 4R,6S-pyranyl-aldehyde of the formula BIIIa or BIIIb:

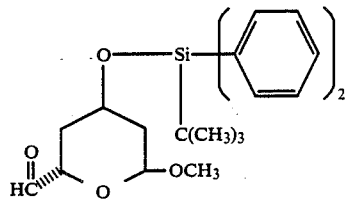

BIIIa

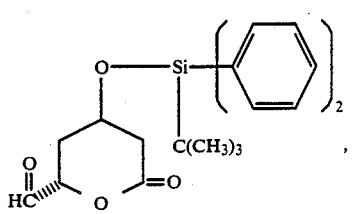

BIIIb corresponding substituted-pyranyl analogs of compounds BII are obtained which can be converted to corresponding lactone final products (I4°) having the 4R,6S form which can be converted to corresponding Compounds I wherein (Z=a), eg I2'''°, having the 3R,5S form. Compounds BIIIa and BIIIb are known and their use in producing olefinic lactones is disclosed in the literature, eg U.S. Pat. No. 4,474,971 and World Patent Application W086/00307 (corresponding to U.S. Pat. No. 4,613,610 (issuing Sept. 23, 1986).

Intermediate derivatives wherein (A=a) and (Z=b) obtained by use of Compounds BIIIa or BIIIb can be converted to corresponding compounds in which (A=b) and (Z=b) by hydrogenating under the conditions of process (g1) described in connection with Reaction Scheme G, above.

Compounds I having one or more of the following characteristics are preferred:
(a) (A=a)
(b) (Z=a) especially having the erythro configuration
(c) when Z=a, $R^8$=M, especially sodium.
(d) (X=a),
(e) and when (A=a) and (Z=a) the optically active isomer of the 3R,5S form.

Reagents and reaction products which are mixtures of stereoisomers (cis, trans and optical) can be separated by conventional means at whatever stage of synthesis is appropriate. Such methods include re-crystallization, chromatography, eg HPLC, formation of esters with optically pure acids and alcohols or of amides and salts with subsequent reconversion with retention of optical purity. For example diastereoisomeric (−)-α-naphthylphenylmethylsilyl derivatives of a lactone type end product of formula I may be separated by conventional means, eg as disclosed in U.S. Pat. No. 4,613,610.

The following examples are illustrative of the invention. All temperatures throughout the specification are centigrade and room temperature (R.T.) is 20 to 30° C., unless indicated otherwise.

Unless indicated otherwise, evaporations are done under reduced pressure, drying of extracts is done over anhydrous sodium sulfate, all ratios of liquid mixtures are volume to volume, and moisture-free solvents and dry nitrogen atmosphere are employed for all reactions which are indicated to be carried out under essentially anhydrous conditions.

As used in these examples, LAH is lithium aluminum hydride, THF is tetrahydrofuran and LDA is lithium diisopropylamide.

Example 1
Ethyl 7-[3-(4-fluorophenyl)-1-isopropyl-1H-pyrrolo-[2,3-b]-pyridin-2-yl]-3,5-dihydroxyhept-6-enoate (erythro)

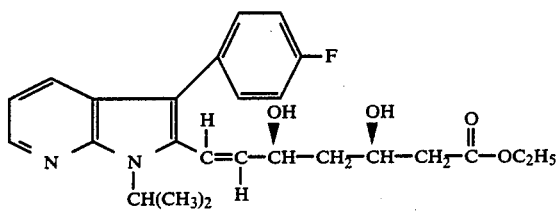

Step 1, 1-(4-fluorophenyl-2-propanone-2-pyridinyl hydrazone

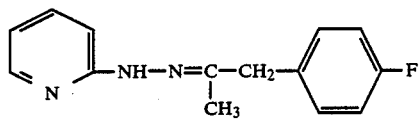

In a vessel fitted with a condenser under nitrogen, 21.8 g (0.2M) of 2-hydrazinopyridine and 30.4 g (0.2M) of (4-fluorophenyl)acetone are heated at 80°-90° for about 30 to 60 mins. Toluene is then added and the mixture refluxed until all water is azeotropically distilled off. The mixture is then evaporated to dryness yielding crude product of this step as a yellow gum. The gum is distilled under reduced pressure (150°-160° at about 50 microns) to obtain the product of this step (as a yellow gum).

Step 2, 3-(4-fluorophenyl)-2-methyl-1H-pyrrolo[2,3-b]-pyridine

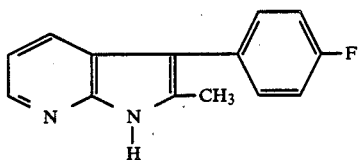

Under nitrogen, 33 g (0.136M) of the hydrazone product of Step 1, above, in 300 ml of diethylene glycol is refluxed (about 250°) for 7 to 8 hrs., and then quenched with water. Solids precipitate and are recovered by filtration. The solids are washed with petroleum ether and taken to near dryness by evaporation, yielding light brown solids. The solids are treated with a large volume of ethyl acetate. Some solids remain which are collected by filtration and dried to yield slightly gray solids (mp 224° to 227°). The filtrate is dried and then treated with charcoal and concentrated until precipitation begins. The solids are collected by filtration, washed with ether/petroleum ether (50/50) yielding yellow solids (m.p. 222° to 226°). The crops of solids are combined to give the title product of this step, for use in Step 3, below. This product may also be called 3-(4-fluorophenyl)-2-methyl-7-azaindole.

Step 3, 1-acetyl-3-(4-fluorophenyl)-2-methyl-1H-pyrrolo [2,3-b]pyridine

Under nitrogen, 4.15 g (0.0184mM) of the azaindole product of Step 2, above, and 100 ml of acetic anhydride are heated at about 100° for about 2 hrs. The mixture is cooled and then evaporated to dryness to obtain a residue. The residue is triturated with ether to give cream-colored solids (mp 84–87°) which are recovered by filtration. The filtrate is evaporated to dryness to give a residue which is dissolved in methylene chloride, filtered through silica and concentrated to yield tan sticky solids, which after trituration with ether/petroleum ether (1:1) yield cream colored solids (mp 84°–86°). Both crops of solids are combined for use in Step 4, below.

Step 4, 1-(1-methyleth-1-enyl)-3-(4-fluorophenyl)-2methyl-1H-pyrrolo[2,3-b]pyridine (a Compound EII)

Under nitrogen, a solution of 0.678 g (0.00253M) of the acetyl product of Step 3, above, 20 ml of abs. toluene (dried over molecular sieves), 1 ml of abs. THF (distilled over LAH) and 2 drops of abs. pyridine is cooled to about −40° and to it is slowly added 5.1 ml of Tebbe Reagent. The resulting mixture is held at about −40° for one half hr., then permitted to warm to R.T. (over 3/4 hr.). 20 ml of ether is then added and the mixture cooled to about 0°. 1 ml of methanol is then added to the mixture dropwise. The resulting mixture is then allowed to stand at R.T. for about 64 hrs.

The mixture is then filtered through Celite, ® then filtered through alumina (Woelm B, Act. I), using ethyl acetate as wash.

The mixture is then evaporated to dryness to yield an orange gum, which is refined by chromatographing on preparative plates developed with ether/petroleum ether (40/60). The main band is eluted with ethyl acetate to give the title product of this step, as slightly yellow solids, mp 84°–87°.

Step 5, 1-isopropyl-2-methyl-3-(4-fluorophenyl)-1H-pyrrolo[2,3-b]pyridine.

Into a parr vessel are placed 330 mg of the olefinic product of Step 4, above, 20 ml of 100% ethanol and 100 mg of 5% palladium on carbon. Hydrogen gas is added at 40 to 50 psi and held at R.T. for about 16 hrs. Ethyl acetate is then added, the mixture filtered through Celite ® and then evaporated to dryness to give the title product of this step as a slightly yellowish gum, which solidified on standing to a light cream solid (mp 57°–68°).

Step 6, 1-isopropyl-2-bromomethyl-3-(4-fluorophenyl)-1H-pyrrolo[2,3-b]pyridine

Under nitrogen is mixed 560 mg (2.09 mM) of the N-isopropyl product of Step 5, above, 40 ml of carbon tetrachloride (dried over molecular sieves), 376 mg (2.09 mM) of N-bromosuccinimide (recrystallized) and 117.4 mg (0.46 mM) of benzoyl peroxide. The mixture is heated at about 80° for 1 hr. under a standard 150 watt incandescent lamp.

The mixture is cooled to R.T., then ether added, and the mixture filtered through a pad of silica gel. The filtrate is then evaporated to dryness to obtain the product of this step as yellow gummy solids which are refrigerated under N₂, until used in Step 7, below.

Step 7, diethyl [[3-(4-fluorophenyl)-1-isopropyl-1H-pyrrolo[2,3-b]pyridin-2-yl]methyl]phosphonate

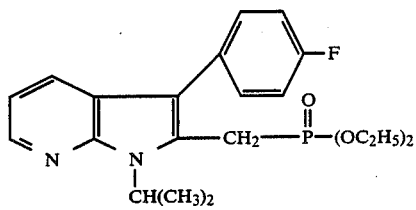

Under nitrogen, 0.950 g of the bromo-product of Step 6, above, in 10 ml of triethyl phosphite is heated at about 140° for about 4 hrs.

The mixture is then cooled and evaporated to dryness to yield 1.373 mg of crude product which is refined by chromatography (prep plates), developed with petroleum ether/ether (60/40) yielding a main band which then is eluted with ethyl acetate to obtain the title product of this step as a yellow gum.

Step 8, ethyl 7-[3-(4-fluorophenyl)-1-isopropyl-1H-pyrrolo[2,3-b]pyridin-2-yl]-3,5-di-(diphenyl-t.butylsilyloxy)hept-6-enoate (erythro)

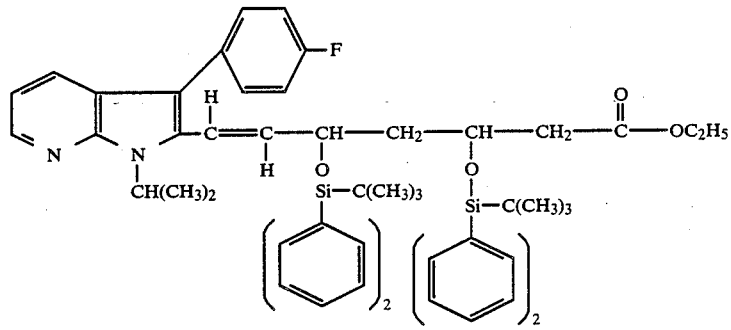

Under nitrogen, 232 mg (0.574mM) of the phosphonate reagent of Step 7, above, in 12 ml of abs. THF is cooled to about −20° to −30° and there is added thereto 0.362 ml (0.688mM) of 1.9M LDA (in cyclohexane), and the mixture stirred for one-half hour. There is then added 470.5 mg (0.724mM) of ethyl erythro-3,5-di-(diphenyl-t-butylsilyloxy)-6-oxohexanoate in 15 ml of abs. THF. The mixture is stirred for about 45 mins. at about −30°.

The mixture is then quenched with saturated aq. ammonium chloride, extracted with ethyl acetate, the extract dried, filtered through a pad of silica gel, and evaporated to dryness to obtain crude title product of this step as a residue (orange gum). The residue is refined by chromatography (prep. plates) developed with petroleum ether/ether (60:40). The second of the 3 main bands (the largest) is eluted with ethyl acetate to yield the title product of this step as a light greenish-yellow gum.

Step 9, ethyl 7-[3-(4-fluorophenyl)-1-isopropyl-1H-pyrrolo[2,3-b]pyridin-2-yl]-3,5-dihydroxyhept-6-enoate (erythro)

Under nitrogen, a mixture of 0.575 g (about 0.628mM) of the protected product of Step 8, above, in 30 ml of abs. THF (dist. over LAH), 2.5 ml (2.5mM) of tetrabutylammonium fluoride (1M in THF) and 0.14 ml (2.5mM) of glacial acetic acid is stirred at R.T. for about 18 hrs. The mixture is taken to dryness to yield crude title product of this example as a dark gum, which is refined by chromatography (prep. plates) developed with methylene chloride/methanol (95:5). The main band is eluted with ethyl acetate to yield the title product of this example as light yellow solids mp. 120°-123° (about 97% erythro).

EXAMPLE 2

Ethyl 7-[3-(4-fluorophenyl)-1-methyl-1H-pyrrolo[2,3-b]pyridin-2-yl]-3,5-dihydroxy-hept-6-enoate, erythro.

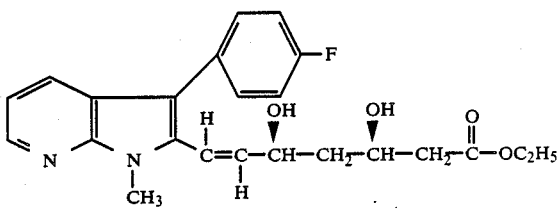

Step 1, 1-(4-fluoro phenyl)-2-ethanone, 2-pyridylhydrazone

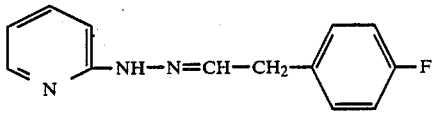

In a vessel, equipped with a Dean-Stark trap, under an atmosphere of nitrogen gas, approximately 16 g (0.116M) of 4-fluorophenylacetaldehyde and 12.6 g (0.116M) of 2-hydrazinopyridine are heated to about 80° to 90° for from 30 to 60 minutes. Toluene is then added and the reaction mixture refluxed with a Dean-Stark trap until all water is removed (about 4 hrs.). This results in a yellow-orange solution which is evaporated (under vacuum) to dryness, yielding the title product of this step as an orange viscous liquid.

Step 2, 3-(4-fluorophenyl)-1H-pyrrolo[2,3-b]pyridine

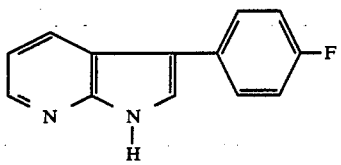

In a vessel, under nitrogen, about 27 g of the crude product of Step 1, above, in about 300 ml of diethylene glycol is refluxed (at about 250°) for about 7 hours. The contents are cooled, and then quenched with water yielding a yellow precipitate. The precipitate is washed thoroughly with water, then once with petroleum ether. The product is dissolved in ethyl acetate, dried and then concentrated by evaporation until precipitation begins. The precipitate is recovered by filtration, and washed first with cold ethyl acetate, then with petroleum ether yielding the title product of this step as yellow solids (mp 190°-192°).

Step 3, 1-methyl-3-(4-fluorophenyl)-1H-pyrrolo[2,3-b]pyridine

Into a vessel under nitrogen is added 0.48 g (10mM) of a 50% dispersion of sodium hydride (in paraffin), 40 ml of absolute xylene (dried over molecular sieves), and 1.94 g (10mM) of the azaindole product of Step 2 above. The mixture is refluxed for 3 hours, then allowed to cool to room temperature. Then there is added slowly 2.82 g (20mM) of methyl iodide in 10 ml of absolute xylene (dried over molecular sieves), and the mixture refluxed for about 2 hours.

Ethanol is then cautiously added to the reaction mixture (to decompose unreacted hydride). The mixture is then cooled, and the xylene solution is extracted with 2N hydrochloric acid (some suspension occurs which is eliminated by filtering). The aqueous acid (containing the reaction product)is made basic and the product extracted with ethyl acetate. The ethyl acetate extract is dried and then evaporated to dryness to obtain a brown gum. The gum is dissolved in methylene chloride to which is added a small amount of anhydrous sodium sulfate and charcoal and then filtered through silica gel, eluting with methylene chloride, to obtain the title product of this step as light tan solids (mp 95°-98°).

Step 4, 1-methyl-2-formyl-3-(4-fluorophenyl)-1H-pyrrolo[2,3-b]pyridine

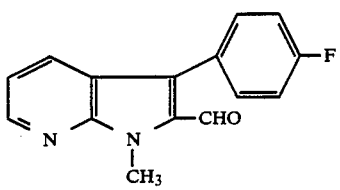

To a vessel, under nitrogen, is charged 1.05 g (4.65 mM) of the product of Step 3, above, in 65 ml of absolute THF (distilled over lithium aluminum hydride), and the solution cooled to about −40° to −50°. 3.53 ml (5.61 mM) of n-butyllithium (1.6 molar in hexane) is added slowly to the reaction mixture at about −40° to −50° and the mixture held at that temperature for 1 hour. (A reddish color develops.) 3.2 ml of dry ethyl formate (97%) (dried over molecular sieves) is added at about −40° to −50°, and the mixture stirred for 2 hours; the color of which lightens to yellow. The mixture is then allowed to warm to R.T. and held for about 16 hours. Saturated aqueous ammonium chloride is then added to quench the reaction mixture, which is then extracted with ethyl acetate. The extract is dried, and then evaporated to dryness to obtain a residue. The residue is refined by chromatography (prep. plates) developed with methylene chloride. The fastest moving heavy band contains the product of this step and is recovered as yellow solids by eluting with ethyl acetate (the second band contains starting material).

Step 5, 3-[1-methyl-3-(4-fluorophenyl)]pyrrolo[2,3-b]pyridin-2-yl]prop-2-enal

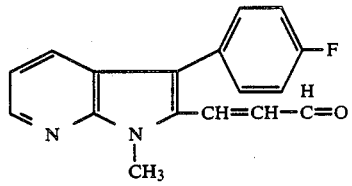

Under a nitrogen atmosphere, 0.302 mg (2.0 mM) of cis-1-bromo-2-ethoxyethylene (purity 95%) in 15 ml of abs. THF (distilled over LAH) is cooled to about −70° and added thereto is 2.35 ml (4.0 mM) of t.butyl-lithium (1.7M in pentane). The mixture is stirred at about −70° for 2 hours. 254 mg (1.0 mM) of the product of Step 4, above, in 10 ml of abs. THF (distilled over LAH) is then slowly added. The mixture is stirred at about −70° for 2 to 3 hours, then while cooling, quenched with saturated aqueous ammonium chloride. Water is added and the mixture extracted with ethyl acetate. The extract is dried and then evaporated to dryness to give an intermediate product as a yellow gum, which is charged to a mixture of about 50 ml of 90% aqueous THF and 75 mg of p-toluenesulfonic acid monohydrate.

The mixture is stirred for about 16 hours resulting in a solution, which is then quenched with 10% aq. sodium bicarbonate, and extracted with ethyl acetate. The extract is dried, and then evaporated to dryness to give a yellow gummy foam, which is then chromatographed on prep. plates developed with petroleum ether/ether (50/50). The main band is eluted with ethyl acetate, the crude material recovered, and upon trituration with ether/petroleum ether (50:50) gives the title product of this step as yellow solids, mp. 155°-160°.

Step 6, ethyl 7-[3-(4-fluorophenyl)-1-methyl-1H-pyrrolo[2,3-b]pyridin-2-yl]-5-hydroxy-3-oxohept-6-enoate

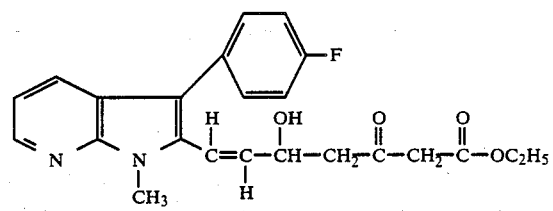

A dianion reagent (a AIII) is prepared by mixing, under nitrogen, 15 ml of abs. THF (distilled over LAH) 3.6 ml (25.36 mM) of diisopropylamide (distilled over LAH), cooling to 0°, and adding 16.2 ml 25.92 mM) of 1.6M n-butyllithium (in hexane). After 15 minutes, the mixture is cooled to −30 to −40°, and there is added 1.5 ml (12 mM) of ethyl acetoacetate (distilled), and the mixture stirred at −30 to −40° for 1 hour.

10 ml of the dianion solution is added, at −30° to −40°, to 0.100g (0.357 mM) of the olefinic aldehyde of Step 5, above, in 10 ml of THF (dist. over LAH) and the mixture stirred at −30° to −40° for 2 hours.

The reaction mixture is quenched with saturated aqueous ammonium chloride (while still cooling), then water added and extracted with ethyl acetate. The ethyl acetate solution is dried and then taken to dryness to give a yellow orange viscous liquid which is chromatographed on prep. plates, developed with methylene chloride/methanol (98/2) and elution of the major band with ethyl acetate to provide the title product of this step as a yellow gum.

Step 7, ethyl 7-[3-(4-fluorophenyl)-1-methyl-1H-pyrrolo[2,3-b]pyridin-2-yl-3,5.dihydroxy hept-6-enoate (erythro)

Under nitrogen, 0.117 g (0.285 mM) of the ketohydroxyester product of Step 6, above, is mixed with 20 ml of abs. THF (distilled over LAH), 5 ml of methanol and 0.371 ml (0.371 mM) of 1M triethyl borane (in THF). 2.3 ml of air is slowly bubbled into the mixture at R.T., then stirred for 2 hours.

The mixture is then cooled to below −75° and in one portion is added 14.7 mg (0.388 mM) of sodium borohydride, and the resulting mixture stirred at below −75° for 3 hours.

To the still cooled mixture is then added 0.2 ml of acetic acid, and the mixture allowed to warm slowly to R.T. over about 16 hours.

The mixture is then slightly cooled and there is added 4 ml of 10% aq. sodium bicarbonate, and the mixture extracted with ethyl acetate. The extract is dried and evaporated to obtain a residue. To the residue is added 10 ml of methanol, and the mixture stirred at R.T. The mixture is then refluxed for 2 hours, and then separated by chromatography (prep. plates developed using methylene chloride/methanol (95:5)). The second major band is eluted using ethyl acetate, and on removing solvent, yields the title product of this example, as a yellow gum.

EXAMPLE 3

Sodium 7-[3-(4-fluorophenyl)-1-methyl-1H-pyrrolo[2,3-b]pyridin-2-yl-3,5-dihydroxy-hept-6-enoate (A) To a solution of 43 mg (0.104 mM) of the product of Example 2, above, in 15 ml of ethanol, is added, at R.T., 3 ml of water and 0.099 ml (0.099 mM) of 1N aq. sodium hydroxide, and the mixture stirred for 1 hr. at R.T.

The mixture is evaporated to dryness to obtain a residue, which is dissolved in chloroform, then evaporated to dryness again. The residue is then dissolved in chloroform, dried and evaporated to dryness to give the product of this example, as light yellow-orange sticky solids.

(B) Repeating the procedure of this example, but using as starting material the product of Example 1, above, there is accordingly obtained the corresponding sodium salt.

EXAMPLE 4

1-Isopropyl-2-formyl-3-(4-fluorophenyl)-1H-pyrrolo[2,3-b]pyridine

Step 1, 1-isopropyl-2-dibromomethyl-3-(4-fluorophenyl)1H-pyrrolo[2,3-b]pyridine

Under nitrogen, 0.536 g (2.0 mM) of 1-isopropyl-2-methyl-3-(4-fluorophenyl)-1H-pyrrolo[2,3-b]pyridine (obtainable by Step 5 of Example 1, above) in 40 ml of carbon tetrachloride (dried over molecular sieves), 1.28 g (7.1 mM) of N-bromosuccinimide (recrystallized) and 0.048 g (0.2 mM) of benzoyl peroxide are refluxed for 2 hours under a 150 Watt light. The mixture is then cooled, solids filtered off, and then evaporated to dryness to obtain the title product of this step as a yellow sticky solid which is used directly for the next step.

Step 2, 1-isopropyl-2-formyl-3-(4-fluorophenyl)-1H-pyrrolo[2,3-b]pyridine 1 g of the product of step 1, above, in 35 ml of 100% ethanol is mixed with 0.4g of calcium carbonate (powdered) and 15 ml of water. The mixture is refluxed for about 4 hours, then cooled, quenched with water and extracted with ethyl acetate. The extracts are dried and then evaporated to dryness to yield a dark amber gum, which is chromatographed on prep. plates, using petroleum ether/ether (85/15) and the largest (second of three) major band eluted with ethyl acetate to obtain the title product of this example as yellow solids, mp 95°–101°.

EXAMPLE 5

Ethyl 7-[3-(4-fluorophenyl)-1-isopropyl-1H-pyrrolo[2,3-b]pyridin-2-yl]-3,5-dihydroxy-hept-6-enoate, erythro Following the procedure of steps 5 to 7 of Example 2, above, but using as starting material the 2-formyl product of Example 4, above, there is accordingly obtained the title product of this example. The corresponding sodium salt may be obtained by hydrolysis with, e.g. sodium hydroxide.

EXAMPLE 6

Ethyl(E)7-[3-(4-fluorophenyl)-1-isopropyl-1H-pyrrolo[3,2-c]pyridin-2-yl]-3,5-dihydroxy-hept-6-enoate (erythro)

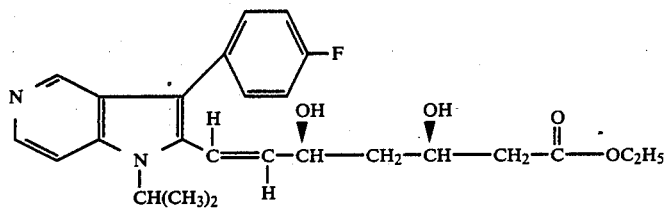

Step 1, 4-hydrazinopyridine HCl 6.56 g (0.0437M) of 4-chloropyridine HCl and 25 ml of ice-cold sodium hydroxide (2N) are mixed and extracted with ether. The solution is dried over $Na_2SO_4$, filtered and evaporated to dryness to produce a light yellow oil. This is added to 7.5 g (0.15M) of $NH_2NH_2 \cdot H_2O$ in 15 ml of absolute ethanol, and heated at 100° for 16 hours in a sealed vessel. After cooling, the mixture is evaporated to dryness, ethanol added and re-evaporated to dryness to produce the title product as light green solids.

Step 2, 1-(4-fluorophenyl)-2-ethanone, 4-pyridylhydrazone 1.455 g (10mM) of the title product of Step 1, above, 1.38 g (10mM) of p-fluorobenzaldehyde and 0.164 g (20mM) of anhydrous sodium acetate are heated at 80°-90° for 30 to 60 minutes. Toluene is added and water azeotropically distilled off for 4 hours. While still warm the insoluble solids are filtered off, washed with $CH_2Cl_2$ and dried. The filtrate is evaporated to dryness, the residue dissolved in $CH_2Cl_2$ and filtered through silica gel, using first $CH_2Cl_2$ and then $CH_2Cl_2/CH_3OH$ (95:5), to yield the title product as a brown gum.

Step 3, 3-(4-fluorophenyl)-1H-pyrrolo[3,2-c]pyridine

If the crude product of Step 2, above, is treated in a manner analagous to Example 2, Step 2, above, there is correspondingly obtained the title product of this step as a dark red gum.

Step 4, 1-benzenesulfonyl-3-(4-fluorophenyl)-1H-pyrrolo[3,2-c]pyridine 106 mg (0.5mM) of the product of Step 3, above, in 5 ml of absolute THF is cooled to −78°. 0.328 ml (0.525mM) of 1.6M n-butyllithium in hexane is added and the mixture stirred for 1 hour whilst allowing the temperature to rise to 0°. The mixture is then re-cooled to −60° and 97mg (0.55mM) of benzenesulfonyl chloride is added. After allowing to warm to RT overnight, the mixture is quenched with aqueous $NaHCO_3$ and extracted with ethyl acetate. After washing with $NaHCO_3$ the mixture is dried over $Na_2SO_4$ and evaporated to dryness. The residue is triturated with ether and the solids produced precipitated and dried to produce the title product of this step.

Step 5, 1-benzenesulfonyl-2-formyl-3-(4-fluorophenyl)-1H-pyrrolo[3,2-c]pyridine 35.2mg (0.1mM) of the product of Step 4, above, in 4ml of absolute THF is cooled to −40° to −50°. To this is then slowly added 0.075ml (0.12mM) of n-butyllithium (1.6M in hexane) and the mixture stirred for 1 hour at −40° to −50°. 0.1 ml (1.2mM) of ethyl formate is added with stirring for 2 hours at −40° to −50°. The mixture is quenched with aqueous ammonium chloride and extracted with ethyl acetate. The resulting solution is dried over $Na_2SO_4$ and evaporated to dryness. The resulting product is applied to prep plates in $CH_2Cl_2/CH_3OH$ (98:2) and the bands eluted with ethyl acetate to give the title product of this step as a yellow gum.

This product may be reacted according to reaction steps h-4 through h-9 in Reaction Scheme H and then process b1 in Reaction Scheme B to produce the title product of this example. The corresponding sodium salt may be obtained by hydrolysis with, e.g. sodium hydroxide.

EXAMPLE 7

(E)-7-[3-(4-fluorophenyl)-1-isopropyl-1H-pyrrolo[3,2-b]pyridin-2-yl]-3,5-dihydroxyhept-6-enoic acid, 1,1-dimethylethyl ester[R-(R*,S*)]

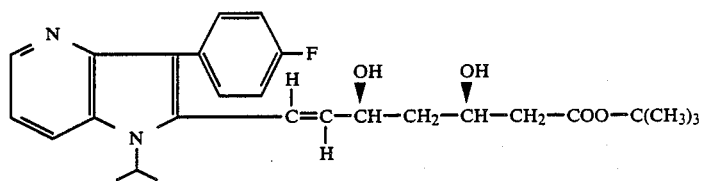

Step 1, 1,1'-[thiobis(methylene)]bis[4-fluorobenzene]

500 ml absolute ethanol, 41 gm (0.172M) sodium sulfide nonahydrate and 50 gm (0.35M) 4-fluorobenzyl chloride are heated slowly to reflux and refluxed for 16 hours. The mixture is then cooled, added to water and extracted with ethyl acetate. The extract is evaporated to dryness over anhydrous sodium sulphate to yield the title product as an oil.

Step 2, 2-[(4-fluorophenyl)(4-fluorophenylmethylthio)]methyl-3-pyridinamine 1.2 g (0.013M) of 3-aminopyridine and 55ml of dry methylene chloride are cooled to −65°. 1.4 g (0.013M) t-butyl hypochlorite is added dropwise over 5 minutes and the mixture stirred for 25 minutes, maintaining the temperature at −65°. Dropwise over 5 minutes is added 3.2 g of the product of Step 1 above, with stirring for 40 minutes, until the reaction mixture turns dark brown. In an oil bath is added a solution of 1.4 g (0.026M) sodium methoxide in 9ml methanol. The temperature is maintained at −65° for 1 hour, and then the mixture is heated to 40° and maintained for 16 hours. The reaction mixture is cooled and added to cold water, before extraction with methylene chloride, drying and reduction to a crude brown oil. The crude product is then column chromatographed on silica gel to obtain the title product (mp 114° to 116.5°).

Step 3, 2-(4-fluorophenyl)-methyl-3-pyridinamine

Under dry nitrogen 17g of the product of Step 2, above, and 500 ml of absolute ethanol are heated over 30 minutes to 40 °. The mixture is cooled to RT, 22 g activated Raney Nickel is added and heated slowly to 40°. After 4 hours the mixture is filtered through celite and the volume reduced to dryness to produce the title product as a crude brown oil.

Step 4, N-[2-(4-fluorophenyl)-methyl-pyridin-3-yl] acetamide 10.44 g of the product of Step 3, above, and 40 ml of acetic anhydride are warmed slowly to 40° for 2 hours. The mixture is added to water, extracted with ethyl acetate, dried and reduced in volume. Petroleum ether is added to achieve the title product (mp 165° to 167°)

Step 5, 3-(4-fluorophenyl)-2-methyl-1H-pyrrolo[3,2-b]pyridine 1 g of the product of Step 4, above, 60 ml Dowtherm and 1.2 g of phosphorus pentoxide are heated to reflux for 45 minutes. The mixture is cooled to RT, 27 ml of methanol added and stirred for 1 hour. 60 ml of 2 N hydrochloric acid is added, the mixture stirred for 1 hour and extracted with ether. The extract is filtered, the aqueous layer acidified, ice added and then 2 N sodium hydroxide is added until the mixture is basic. After methylene chloride extraction, drying, evaporation to dryness and chromatography, the title product is produced (mp 199° to 206°).

If the product of Step 5, above, is taken through steps analogous to those of Example 1, Steps 3 to 7, the following products may be obtained:

Step 6, 1-[3-(4-fluorophenyl)-2-methyl-1H-pyrrolo[3,2-b]pyridin-1-yl]ethanone (mp 122° to 127°)
Step 7, 3-(4-fluorophenyl)-2-methyl-1-(1-methylethenyl)-1H-pyrrolo[3,2-b]pyridine (thick yellow oil)
Step 8, 3-(4-fluorophenyl)-2-methyl-1-isopropyl-1H-pyrrolo[3,2-b]pyridine (mp 153° to 157°)
Step 9, 2-bromomethyl-3-(4-fluorophenyl)-1-isopropyl1H-pyrrolo[3,2-b]pyridine
Step 10: [3-(4-fluorophenyl)-1-isopropyl-1H-pyrrolo[3,2-b]pyridin-2-yl]methyl-diethyl ester phosphoric acid
Step 11: 7-[3-(4-fluorophenyl)-1-isopropyl-1H-pyrrolo[3,2-b]pyridin-2-yl]-3,5-di[(1,1-dimethylethyl) diphenylsilyloxy]-6-heptenoic acid 1,1-dimethylethylester[R-(R*S*)]

To 13 mg (0.13M) of diisopropylamide and 2ml of dry THF is added 0.08 ml (0.13mM) n-butyllithium at 0–5°. After 15 minutes, 49mg (0.12mM) of the product of Step 10, above, in dry THF is added at −35°, stirred for 2 hours and the temperature is allowed to rise −10°. The mixture is cooled to −30° and 104 mg (0.15mM) of [R-(R*S*)]-3,5-di[-(1,1-dimethylethyl)diphenylsilyloxy]6-oxohexanoic acid-1,1-dimethylethylester in a minimum volume of THF is added. The reaction mixture is stirred for 16 hours and the temperature allowed to rise to RT before being added to saturated ammonium chloride and extracted with ethyl acetate. The organic layers are dried, reduced to dryness, and chromatographed to obtain the title product as a thick yellow oil.

Step 12, 7-[3-(4-fluorophenyl)-1-isopropyl-1H-pyrrolo[3,2-b]pyridin-2-yl]-3,5-dihydroxy-6-heptenoic acid 1,1-dimethylethylester [R-(R*S*)]

(A) Using the product of Step 11, above, and employing methods analogous to those of Example 1, Step 9, above, the title product of this example may be obtained. (mp 62°–65°).

(B) Using the product of Step 12A, and employing methods analogous to those of Example 3A, above, the corresponding sodium salt is obtained.

EXAMPLE 8

(E)7-[3-(4-fluorophenyl)-1-isopropyl-1H-pyrrolo[3,2-b] pyridin-2-yl]-3,5-dihydroxy-1,1-dimethylethylester [R-(R*S*)]-6-heptenoic acid hydrochloride To 4 ml of absolute ether is added 25 mg (0.053mM) of the product of Example 7, above, at RT. To this mixture is added 190 mg (5.3mM) of anhydrous hydrochloric acid. Filtering produces the title product of this example as a light yellow crystalline solid (mp 118° to 122°).

Repeating the procedure of this example, but using as starting material the product of Example 1, above, and likewise with the product of Example 2, above, there may be obtained the corresponding hydrochloride salts thereof.

EXAMPLE 9

3R,5S Ethyl 7-[3-(4-fluorophenyl)-1-isopropyl-1H-pyrrolo[2,3-b]-pyridin-2-yl]-3,5-dihydroxyhept-6-enoate and its sodium salt

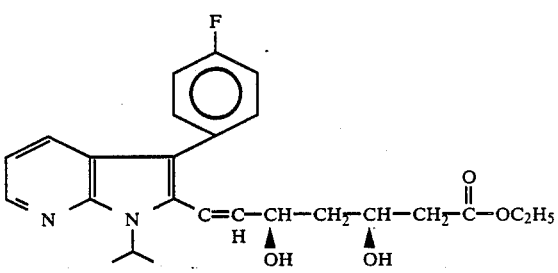

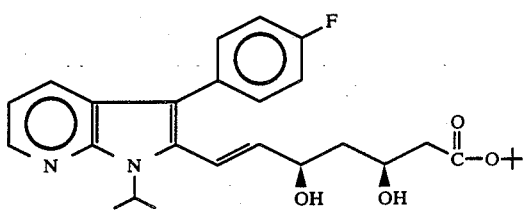

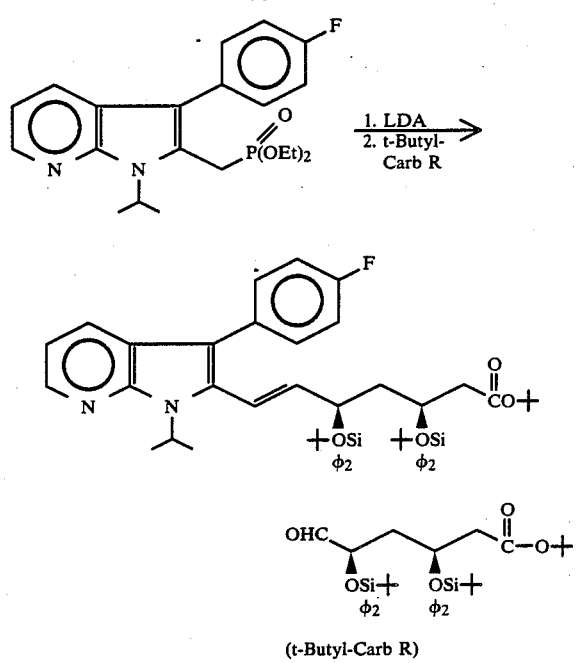

(t-Butyl-Carb R)

Step 1

345 mg (0.853 mM) of the compound of Example 1, Step 7, is added to 10 ml absolute THF. This is cooled to −20 to −30° C. and 0.68 ml (1.03 mM) of 1.5M LDA solution in cyclohexane is added dropwise over approximately 1 minute. The temperature is maintained at −20° to −30° while the solution is stirred for 30 minutes. The resultant amber-colored solution is then cooled to −40° while the solution is then cooled to −40° while 746 mg (1.075 mM) of t-Butyl Carb R (structure depicted above) in 10 ml absolute THF is added dropwise, but rapidly. After the addition is complete, the color lightens to bright yellow, and this solution is stirred for 1.5 hours.

(t-Butyl Carb-R may be prepared according to the method described in co-pending Ser. No. 07/166,594 filed Mar. 10, 1988 now U.S. Pat. No. 4,870,199, issued Sept. 26, 1989 which is hereby incorporated by reference).

While still cold, the reaction is quenched with saturated NH4Cl. It is then extracted with EtOAc. The product is dried over Na2SO4 and evaporated to yellow foam-like solids. The solids are refined by prep plate chromatography using 80:20 petroleum ether:ether. The result is colorless foam-like solids.

Step 2

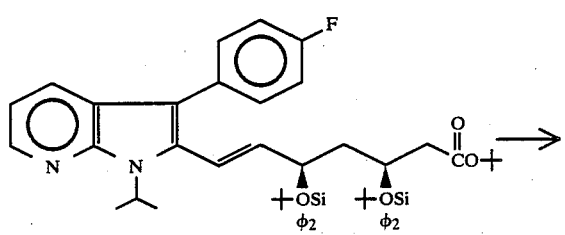

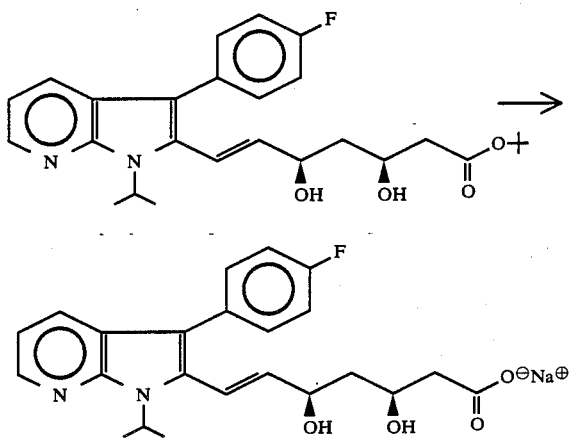

0.9465 g (3 mM) tetrabutylammonium floride tetrahydrate (Fluka), 10 ml acetonitrile, and 0.6 g (0.57 ml, 3mM) galcial acetic acid are combined and heated to 50° C. To this is added dropwaise 0.2832 g (0.3 mM) of the product of Step 1 in 3 ml acetonitrile. The mixture is heated to 50°-60° C. for 5 days, stirring constantly. The resultant dark amber-colored solution is allowed to cool to room temperature and is then quenched with 10% aq. NaHCO3. It is extracted with EtOAc, dried over Na2S4 and evaporated to dryness yielding an amber gum.

The gum is purified using prep plate chromotography with 98:2 CH2Cl2:MeOH. The result upon standing is a yellow gum.

Step 3

8.18 g (17.48 mM) of the product of Step 2 is combined with 200 ml 100% EtOH and 20 ml H2O, and then cooled in an ice bath. To this, 17.13 ml (17.13 mM) IN Aq. NaOH is added slowly. The resulting solution is stirred at room temperature for 3 hours, and then evaporated to dryness. The product is dissolved in CH3Cl3, dried over Na2SO4 and evaporated to dryness, yielding yellow foam-like solids.

The solids are re-dissolved in CHCl3, re-dried over Na2SO4, then filtered and evaporated to a small volume (approx. 50 ml). Then, while stirring under a N2 blanket, ether is added to precipitate light yellow solids, which are quite hygroscopic and not amenable to filtration. They are re-dissolved in CHCl3 and evaporated to dryness, yielding 7.5 g of light yellow solids.

EXAMPLE 10

The following data were obtained for the preceding compounds. Unless otherwise stated the data are NMR spectra measured at 200 mHz. Shifts are in ppm. relative to tetramethylsilane.

Abbreviations:

| | |
|---|---|
| s = | singlet |
| d = | doublet |
| dd = | doublet of a doublet |
| t = | triplet |
| q = | quartet |
| Q = | quintet |
| m = | multiplet |
| br = | broad |
| bs = | broad singlet |
| dq = | doublet of a quartet |
| dt = | doublet of a triplet |

| Example No. | |
|---|---|
| 2 | CDCl$_3$: 1.28(t,3H); 2.50(d,2H); 3.70(d,2H); 3.96(s,3H); 4.17(q,2H); 4.28(M,1H); 4.53(m,1H); 6.05(q,1H); 6.74(q,1H); 7.10(m,3H); 7.40(m,2H); 7.80(m,1H); 8.32(m,1H); |
| 3A | CD$_3$OD: 2.33(m,2H); 3.30(m,2H); 3.93(s,3H); 4.02(m,1H); 4.42(m,1H); 6.10(q,1H); 6.76(q,1H); 7.17(m,3H); 7.46(m,2H); 4.87(m,1H); 8.23(m,1H). |
| 3B | CD$_3$OD: 1.71(d,6H); 2.30(m,2H); 3.94(m,1H); 4.39(m,1H); 5.13(m,1H); 5.80(q,1H); 6.75(q,1H); 7.11(m,3H); 7.43(m,2H); 7.78(m,1H); 8.20(m,1H). |
| 7 Step 12A | CDCl$_3$: 1.45(s,9H); 1.50(m,2H); 1.65(m,6H); 2.39(d,2H); 3.92(s,1H); 3.98(s,1H); 4.20(m,1H); 4.52(m,1H); 4.86(m,1H); 5.91(q,1H); 6.75(q,1H); 7.10(m,3H); 7.57(m,2H); 7.80(m,1H); 8.45(m,1H). |
| 7 Step 12B | CD$_3$OD: 1.57(m,2H); 1.68(d,6H); 2.30(m,2H); 3.97(m,1H); 4.42(m,1H); 5.00(m,1H); 5.85(q,1H); 6.75(q,1H); 7.18(m,3H); 7.51(m,2H); 8.09(m,1H); 8.25(m,1H). |

What is claimed is:
1. A compound of the formula I:

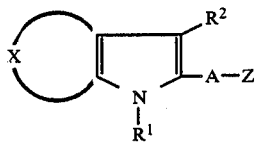

wherein
X is

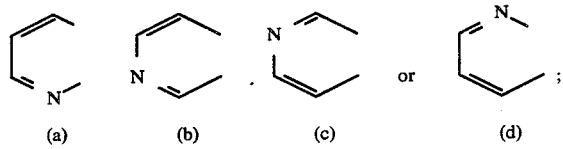

$R^1$ is a primary $C_{1-6}$alkyl not containing an asymmetric carbon atom or isopropyl;
$R^2$ is (a)

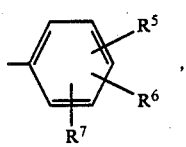

(b) a primary or secondary $C_{1-6}$alkyl not containing an asymmetric carbon atom, (c) $C_{3-6}$cycloalkyl or (d) phenyl—$(CH_2)_m$—, wherein
$R^5$ is hydrogen, $C_{1-3}$alkyl, n-butyl, i-butyl, t-butyl, $C_{1-3}$alkoxy, n-butoxy, i-butoxy, trifluoromethyl, fluoro, chloro, phenoxy or benzyloxy;
$R^6$ is hydrogen, $C_{1-3}$alkyl, $C_{1-3}$alkoxy, trifluoromethyl, fluoro, chloro, phenoxy or benzyloxy;
$R^7$ is hydrogen, $C_{1-2}$alkyl, $C_{1-2}$alkoxy, fluoro or chloro; and
m is 1, 2 or 3;
with the provisos that not more than one of $R^5$ and $R^6$ is trifluoromethyl, not more than one of $R^5$ and $R^6$ is phenoxy, and not more than one of $R^5$ and $R^6$ is benzyloxy;

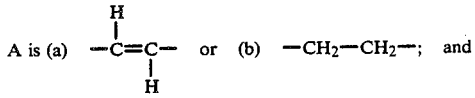

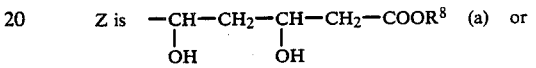

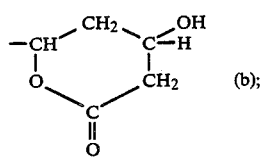

in which $R^8$ is hydrogen, $R^9$ or M,
wherein
$R^9$ is a physiologically acceptable and hydrolyzable ester group, and
M is a pharmaceutically acceptable cation.
2. A compound of claim 1 in which X is of type (a).
3. A compound of claim 2 in which $R^2$ is of type (a).
4. A compound of claim 3 in which $R^2$ is selected from the group consisting of phenyl, p-fluorophenyl and 3,5-dimethylphenyl.
5. A compound of claim 2 in which $R^1$ is a primary alkyl.
6. A compound of claim 5 in which $R^1$ is methyl.
7. A compound of claim 2 in which $R^1$ is isopropyl.
8. A compound of claim 2 in which A is of type (a).
9. A compound of claim 1 in which X is of type (b).
10. A compound of claim 9 in which $R^2$ is of type (a).
11. A compound of claim 9 in which A is of type (a).
12. A compound of claim 1 in which X is of type (c).
13. A compound of claim 12 in which $R^2$ is of type (a).
14. A compound of claim 12 in which A is of type (a).
15. A compound of claim 1 in which X is of type (d).
16. A compound of claim 15 in which $R^2$ is of type (a).
17. A compound of claim 16 in which $R^2$ is selected from the group consisting of phenyl, p-fluorophenyl, and 3,5-dimethylphenyl.
18. A compound of claim 15 in which $R^1$ is a primary alkyl.
19. A compound of claim 18 in which $R^1$ is methyl.
20. A compound of claim 15 in which $R^1$ is isopropyl.
21. A compound of claim 15 in which A is of type (a).
22. A compound of claim 1 in which $R^8$ is hydrogen.
23. A compound of claim 1 in which $R^8$ is a physiologically acceptable and hydrolyzable ester group.
24. A compound of claim 1 in which $R^8$ is a pharmaceutically acceptable cation.
25. A compound of claim 2 in which $R^1$ is isopropyl;
$R^2$ is p-fluorophenyl;
A is

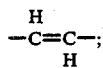

and
Z is of type (a).

26. A compound of claim 25 which is the 3R,5S isomer.

27. A composition useful for treating atherosclerosis in a mammal in need of such treatment comprising an effective amount of a compound according to claim 1 and an inert non-toxic, pharmaceutically acceptable carrier, the amount of compound being an amount effective for inhibiting cholesterol biosynthesis in a mammal.

28. A method of treating atherosclerosis by inhibiting cholesterol biosynthesis comprising administering to a mammal in need of such treatment an amount effective for inhibiting cholesterol biosynthesis of a compound of claim 1.

* * * * *